United States Patent [19]

Pert et al.

[11] 4,251,995

[45] Feb. 24, 1981

[54] METHOD OF FREEZING HUMAN BLOOD PLATELETS IN GLYCEROL-GLUCOSE USING A STATICALLY CONTROLLED COOLING RATE DEVICE

[75] Inventors: James H. Pert, Glenmont; George Dayian, Albany, both of N.Y.

[73] Assignee: Hedbergska Stiftelsen, Stockholm, Sweden

[21] Appl. No.: 33,306

[22] Filed: Apr. 25, 1979

[51] Int. Cl.³ .............................................. F65B 63/08
[52] U.S. Cl. ......................................... 62/60; 62/64; 62/78; 62/341; 220/335
[58] Field of Search .................. 62/1, 60, 64, 78, 341; 220/335

[56] References Cited

U.S. PATENT DOCUMENTS

| | | | |
|---|---|---|---|
| 851,357 | 4/1907 | Keefe | 220/335 |
| 1,032,326 | 7/1912 | Erichsen | 220/335 |
| 1,364,594 | 1/1921 | Thomas | 220/335 |
| 1,624,719 | 4/1927 | Dixon | 206/39 |
| 1,983,768 | 12/1934 | Norton | 62/64 |
| 2,964,920 | 12/1960 | Staebler | 62/1 |
| 3,294,229 | 12/1966 | McConnell et al. | 206/449 |
| 3,875,754 | 4/1975 | Faust et al. | 62/64 |

OTHER PUBLICATIONS

Valdorf-Hansen, J. F. et al: Amer. Jour. of Physiology 1.220, No. 1, 1/1971, USA, *Effect of Temp. & Inhibitors on Serotonin-$^{14}C$ Release from Human Platelets.*
Z. Jerushalmy et al.: *Some Effects of Fibrinogen Degradation Products (FDP) of Blood Platelets*; Amer. Natl. Red Cross Lab., N. Y., pp. 413-419.
Zucker, M. B. et al.: Kinetic Studies of Platelet Aggregation Induced by . . . Adenosine, Amer. Natl. Red Cross Lab., N. Y., pp. 714-725.
White et al.: *An Ultrastructural Basis for the Shape Changes Induced in Platelets by Chilling*, Blood, vol. 30, No. 5 (Nov. 1967), pp. 625-635.
White, J. G.: *The Submembrane Filaments of Blood Platelets*, Amer. J. Path. 56, 267 (1969).
Gaarder, A. et al.: Nature, 192, 531 (1961), *Adenosine Diphosphate in Red Cells as a Factor . . . Blood Platelets.*
Brecher, G. et al.: J. Appl. Physiol. 3 365 (1950): *Morphology and Enumeration of Human Blood Platelets.*
Zucker-Franklin et al.: Jour. Clinical Investigation, vol. 48, 165 (1969), *Microfibrils of Blood Platelets.*
Born, G. V. R. et al.: J. Physiol. (1959) 146, 472–491: *Studies on the Uptake of 5-Hydroxytryptamine by Blood Platelets.*
Pert, J. H. et al.: Cryobiology 16, 90–96 (1979): *Statically Controlled Cooling Rate Device.*
Dayian, G. et al.: Transfusion, May–Jun. 1979, vol. 19, No. 3, *A Simplified Method . . . Cooling Rate.*
Dayian, G. et al.: Cryobiology 13, 1–8 (1976), *Cryopreservation of Human Platelets for Transfusion.*

*Primary Examiner*—Ronald C. Capossela
*Attorney, Agent, or Firm*—Cooper, Dunham, Clark, Griffin & Moran

[57] ABSTRACT

An inexpensive, statically controlled cooling rate device comprising a cassette of metal plates and cardboard insulation in a plastic bag was used to freeze platelets in liquid nitrogen with glycerol-glucose as cryoprotectant. Depending on the thermocouple location, the cooling rate in the freezing bag varied between 22.1° and 38.6° C. per minute, averaging 33.6°±1.1° C. per minute at the center. The post-thaw recovery of platelets frozen with this device and reconstituted in plasma averaged 88.6±11.7 percent, compared to 86.1±9.9 percent for nonfrozen but identically processed platelets. [$^{14}C$]Serotonin uptake after 0.5-hour incubation was 95.9±1.9 percent for fresh platelets in platelet-rich plasma, 92.7±4.4 percent for nonfrozen processed platelets, and 81.4±11.8 percent for frozen platelets, increasing to 85.9±7.7 percent after one-hour incubation.

15 Claims, 2 Drawing Figures

METHOD OF FREEZING HUMAN BLOOD PLATELETS IN GLYCEROL-GLUCOSE USING A STATICALLY CONTROLLED COOLING RATE DEVICE

A method for cryopreservation of human platelets, described earlier, Dayian, G. and Rowe, A. W., *Cryobiology*, 13, 1 (1976), used glucose and glycerol in plasma as the cryoprotective medium. After thawing, the platelet concentrate could be diluted with platelet-free plasma (PFP) so that post-thaw washing was not necessary. The post-thaw yield was quite variable, however, with an average loss of 30 percent.

In the simplified method described herein the average manipulative loss has been reduced to 15 percent. The complex, commercial, controlled cooling rate instrument previously used has been replaced with a simple, inexpensive device. In accordance with the present invention, a freezing bag containing a cellular suspension to be preserved is placed between cardboard insulators, positioned inside hinged metal plates, and then this assembly is covered with another bag, and the whole unit immersed in a freezing medium such as liquid nitrogen. The cooling rate is determined by the thermal characteristics of the components and does not require electronic or mechanical parts as in presently available commercial instruments. As a result, a high degree of reproducibility is achieved, the technical skill required is minimized, and the equipment cost is much reduced.

DETAILED DESCRIPTION OF THE INVENTION MATERIALS AND METHODS

Preparation of Platelet Concentrate

To prepare platelet-rich plasma (PRP), 450 ml of whole blood, collected in CPD anticoagulant, was centrifuged at 1,800 rpm and 22° C. for ten minutes after reaching speed in a Sorvall RC-3 centrifuge with a HG-4 rotor. The PRP was allowed to equilibrate at 23°±1° C., and 10 ml of acidifying solution per 100 g of PRP was added to lower the pH to 6.5. The PRP was then centrifuged for five minutes after reaching a speed of 4,000 rpm, and the supernatant platelet-poor plasma (PPP) was removed. (If red cells were inadvertently carried along with PRP, they were removed by centrifugation of PRP for three minutes after it reached 900 rpm.)

The platelets were resuspended by hand in residual plasma to give approximately 5 ml of concentrate, most of which was transferred by syringe into a platelet freezing bag. The remainder, about 0.5 ml, was recovered by diluting it with 5.5 ml of freezing solution and then added to the freezing bag. The volume of freezing solution was thus adjusted to equal the volume of concentrate. The final volume of glycerolized platelet suspension to be frozen varied between 10 and 12 ml. Ten ml of air was added, and the freezing bag was sealed.

A portion of the PPP was centrifuged at 12,000 rpm in the Sorvall RC-2 for ten minutes to remove residual platelets. This platelet-free plasma (PFP) was frozen for later use in reconstituting thawed platelets.

Assembly and Use of Freezing Cassette

Figure 1:
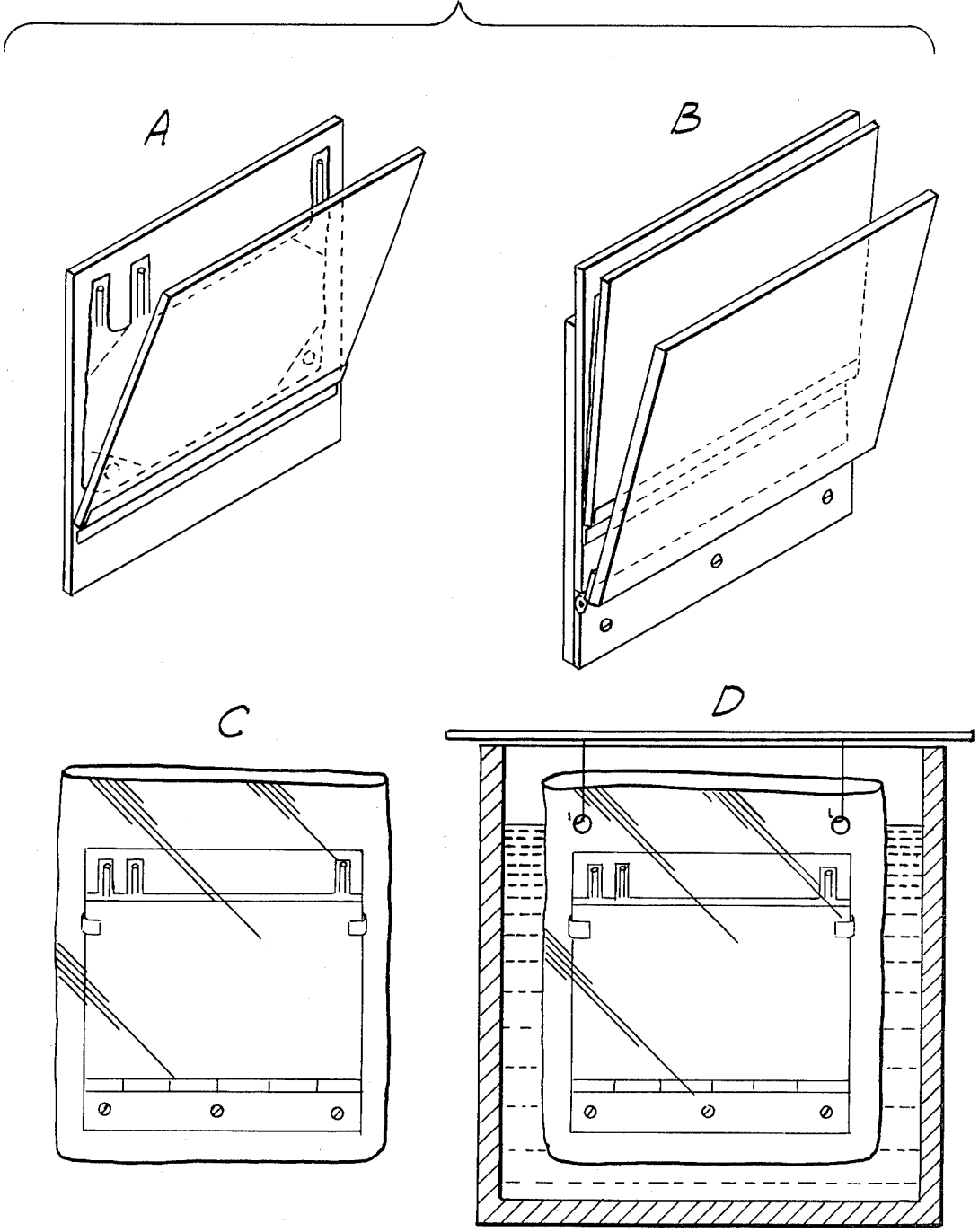
FIG. 1A shows a freezing bag containing platelets between two hinged cardboard sheets.
FIG. 1B shows the assembly of FIG. 1A inserted between two hinged metal plates.
FIG. 1C shows the completed assembly inserted into a plastic bag.
FIG. 1D shows the device of FIG. 1C immersed in a container of liquid nitrogen.

The freezing bag is placed between two sheets of corrugated cardboard (single-wall, bursting strength 19.4 kg/cm$^2$ [275 pounds/inch$^2$], C flute obtained from Longview Fibre Co., Amsterdam, N.Y.). Each sheet measures 13.3 by 15.2 cm; two corners of one sheet are removed to accommodate the bag ports (FIG. 1). The cardboard and freezing bag are then placed between hinged, 0.64-cm-thick aluminum plates, one 12.7×15.2 cm, the other 15.2×15.2 cm (Aluminum type 2024T3, Alcoa, Pittsburgh, Pa.) so as to rest on the flange of the hinge. The plates are taped tightly together at the upper side corners of the metal, and this assembly is placed in an outer plastic bag which measures 25.4×35.6 cm and varies in thickness between 0.01–0.015 cm., e.g., polyethylene bags 10×14 inches, 0.004 inch thick, distributed by Bel-Art, Pequannock, N.J. This unit is submerged for 15 minutes in liquid nitrogen, with the level of liquid nitrogen above the metal plates throughout freezing.

Storage, Thawing and Reconstitution

After freezing, the tapes holding the cassette closed are cut, and the frozen bag of platelets with the cardboard sheets is transferred immediately into the vapor phase of a liquid nitrogen freezer for storage. In these studies, storage time was at least 18 hours.

For use, 50 ml of PFP is thawed, and the pH is adjusted to 6.5, if necessary. Next the freezing bag is removed from its cardboard covers, promptly immersed in water at room temperature (22°–23° C.), and gently agitated by hand. Immediately after the platelets have thawed and warmed to water temperature, 10 ml of the PFP is added slowly by syringe through an entry port while the freezing bag is rocked gently. After 15 minutes rest at room temperature, an additional 20 ml of PFP is added with occasional agitation, and ten minutes later the remaining 20 ml of PFP is added.

Evaluation of Post-Thaw Yield and Function

Platelet yield: To differentiate the processing losses from freeze-thaw injury, the PRP from two units of whole blood of the same ABO type were pooled and then separated into two equal volumes. These preparations were processed similarly, except that one unit was frozen and the other was not. The reconstituted platelet concentrates were diluted with PFP to approximate the platelet number in PRP and were counted in duplicate by two observers, using the method of Brecher and Cronkite, *Appl. Physiol.* 3, 365 (1950). The four readings were averaged. The yields were calculated from the platelet counts and volumes, compared to the total number of platelets in the starting PRP.

Serotonin uptake: Radiolabeled serotonin ([2'-$^{14}$C] hydroxytryptamine creatinine sulphate; 55 mCi/m-mol)* was dissolved in 70 percent alcohol to give a final concentration of 10 μCi/ml and stored at −20° C., according to the method of Jerushalmy, Z. and Zucker, M. B., Thromb. Diath. Haemorrh., 15, 413 (1966). For assay, 0.01 ml of the [$^{14}$C] serotonin was added to 4-ml portions of platelet suspension, which had been held at 37° C. for 30 minutes, and the mixtures were further incubated at 37° C. for 30 minutes to one hour. Radioactivity was determined on samples of platelet suspensions and platelet-free aliquots to determine the percentage of sorotonic taken up.
*obtained from Amersham, Arlington Heights, Ill.

Cooling Rate Determinations

Temperature was monitored with a #30-55-1 copper-constantan thermocouple and a Leeds and Northrup Speedomax W recorder, standardized with the company's millivolt potentiometer, model 8690. The platelet freezing bag with the thermocouple in place contained 10 ml of air and 10 ml of a 1:1 mixture of 0.85 percent NaCl and freezing solution. For this study the cooling rate is defined as the rate in degrees centigrade per minute at the steepest slope after release of the heat of fusion.

Acidifying and Freezing Solutions

One liter of aqueous acidifying solution contained 53.2 g of Na$_3$-citrate (dihydrate), 17.7 g of citric acid (monohydrate), 60.5 g of anhydrous dextrose, and 4.4 g of NaOH.

One liter of aqueous freezing solution contained 100 ml of glycerol (density at 25° C.=1.245 g/ml), 80.0 g of anhydrous dextrose, 11.1 g pf Na$_3$-citrate, and 0.5 g of citric acid (monohydrate).

RESULTS

Figure 2:
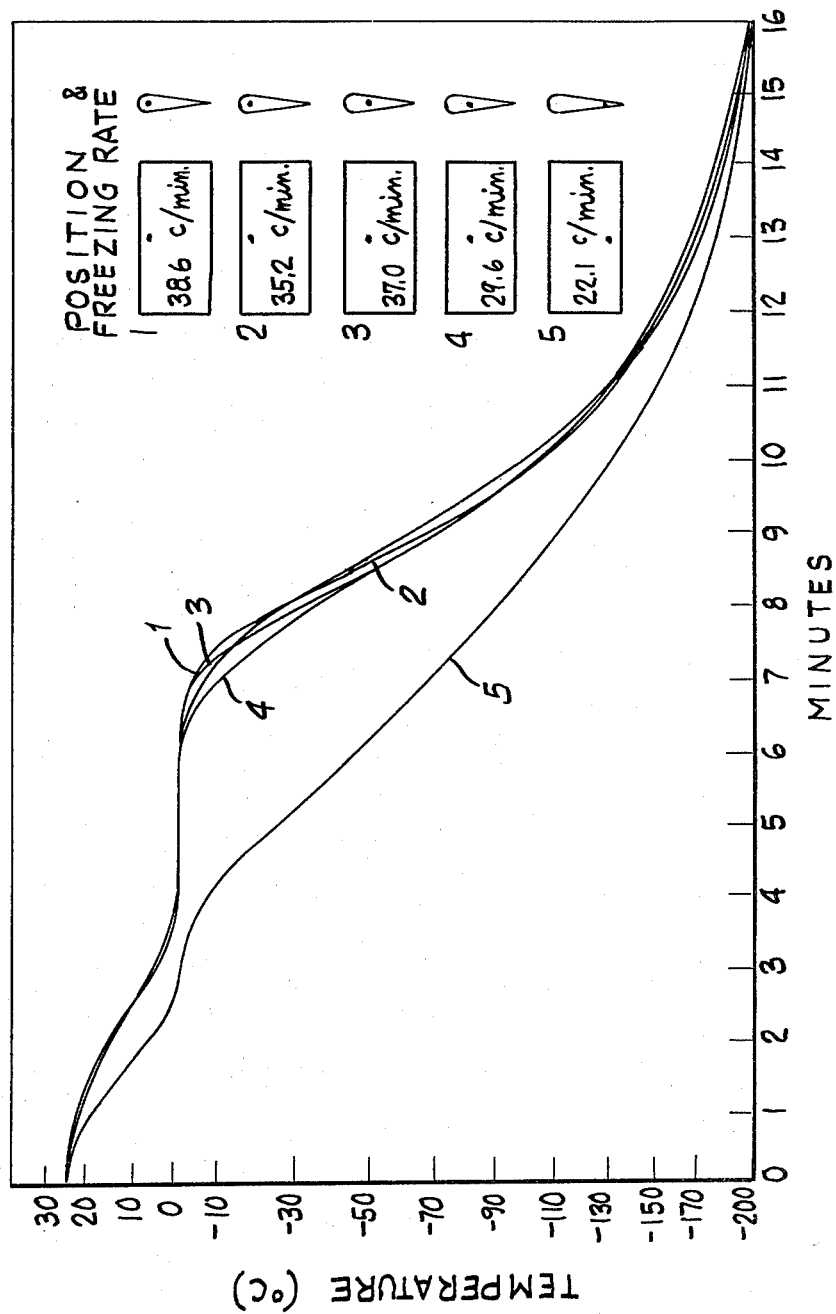
FIG. 2 shows cooling curves obtained for the statically controlled cooling rate device. A copper-constantan thermocouple was placed in the indicated positions with a freezing bag which contained 5 ml of freezing solution, 5 ml of 0.85 percent NaCl, and 10 ml of air.

In blank runs without platelets, a series of cooling curves were obtained with the thermocouple positioned at five different points within the freezing bag, which was filled with 10 ml of freezing solution at final concentrations of 5 percent glycerol and 4 percent glucose. The maximum cooling rates varied from 22.1° to 38.6° C. per minute (FIG. 2). In a separate study of ten replicate determinations with the thermocouple in the center of the freezing bag (position 3) the cooling rate averaged 33.6°±1.1° C. per minute.

Little difference in recovery was indicated by platelet counts of 17 paired samples, processed identically except that only one of each pair was frozen with the new device and then thawed (Table 1). The mean platelet recovery was 86.1±9.9 percent for the nonfrozen units and 88.6±11.7 percent for the frozen units.

TABLE 1.

| Recovery of Platelets as a Percentage of Platelets in PRP | | |
|---|---|---|
| Experiment | Nonfrozen Platelets | Frozen Platelets |
| 1 | 98.7 | 95.1 |
| 2 | 59.7 | 73.9 |
| 3 | 82.8 | 81.9 |
| 4 | 72.0 | 77.6 |
| 5 | 86.1 | 94.0 |
| 6 | 90.1 | 91.7 |
| 7 | 86.2 | 80.8 |
| 8 | 86.8 | 103.0 |
| 9 | 93.6 | 87.6 |
| 10 | 95.5 | 103.0 |
| 11 | 74.7 | 104.0 |
| 12 | 98.6 | 75.1 |
| 13 | 87.0 | 86.0 |
| 14 | 84.9 | 77.8 |
| 15 | 86.0 | 73.6 |
| 16 | 87.4 | 92.1 |

TABLE 1.-continued

| Recovery of Platelets as a Percentage of Platelets in PRP | | |
|---|---|---|
| Experiment | Nonfrozen Platelets | Frozen Platelets |
| 17 | 94.0 | 110.0 |
| Mean ± SD | 86.1 ± 9.9 | 88.6 ± 11.7 |

Pairs of nonfrozen and frozen samples were tested for platelet function by comparing their ability to take up [$^{14}$C] serotonin with that of fresh PRP. After 30 minutes of incubation, uptake by nonfrozen platelet samples was 92.7±4.4 percent, close to that of fresh platelets at 95.9±1.9 percent (Table 2). The uptake by frozen platelets was perceptibly lower at 81.4±11.8 percent, but it increased somewhat to 85.9±7.7 percent when the incubation time was increased to one hour. In one instance the outer bag broke, allowing liquid nitrogen to contact the freezing bag directly. The resulting increase in cooling rate adversely affected platelet function, and this value was omitted from the calculations.

TABLE 2.

| | [$^{14}$C]Serotonin Uptake (%) | | | |
|---|---|---|---|---|
| | Platelet Type (Incubation Time) | | | |
| | Fresh | Nonfrozen | Frozen | |
| Experiment | (0.5 h) | (0.5 h) | (0.5 h) | (1 h) |
| 1 | 96.5 | 96.2 | — | 94.5 |
| 2 | 96.6 | 96.1 | 77.2 | 86.1 |
| 3 | 96.1 | 91.6 | 88.9 | 91.9* |
| 4 | 97.2 | 96.5 | 93.7 | 94.2 |
| 5 | 96.6 | 80.8 | 83.9 | 88.4* |
| 6 | 96.1 | 89.9 | 88.6 | 91.7 |
| 7 | 96.6 | 81.7 | 78.2 | 83.5 |
| 8 | 88.7 | 89.6 | 52.1 | 66.7* |
| 9 | 96.0 | 95.4 | 93.1 | 94.8 |
| 10 | 96.8 | 96.0 | 3.0 | 2.0$^f$ |
| 11 | 99.0 | 96.1 | 89.0 | 93.6 |
| 12 | 96.8 | 96.1 | 70.0 | 76.5 |
| 13 | 96.6 | 96.2 | — | 86.1 |
| 14 | 95.7 | 94.4 | 89.1 | 93.3 |
| 15 | 95.7 | 94.9 | 92.0 | 93.7 |
| 16 | 95.9 | 94.0 | 85.9 | 81.2 |
| 17 | 95.6 | 90.4 | 77.5 | 85.1* |
| 18 | 95.3 | 93.1 | — | —* |
| 19 | 95.4 | 91.2 | 56.2 | 57.0* |
| 20 | 95.4 | 93.9 | 86.9 | 88.8 |
| Mean ± SD | 95.9 ± 1.9 | 92.7 ± 4.4 | 81.4 ± 11.8 | 85.9 + 8.7 |

*Unit aggregated on thawing or reconstitution, irreversibly in Exp. 18
$^f$Outer plastic bag cover broke on freezing; uptake value omitted from calculations (see results).
—Uptake not measured.

DISCUSSION

The functions of the separate components of the freezing cassette may be described briefly as follows. The outer plastic bag improves the heat transfer rate by preventing the formation of an insulating layer of gaseous nitrogen and by protecting the platelet freezing bag from direct contact with liquid nitrogen. The metal plates act as heat sinks, while the cardboard insulators moderate the heat flow from the sample to the metal plates. The cardboard also protects the freezing bag against warming and breakage during storage and retrieval, since the cardboard and bag can be transferred as a unit. The cardboard can be marked for sample identification. Repeated use of the cardboard insulators is not advised, as they tend to soften and change in insulating property.

In its ready-to-freeze position, the platelet bag assumes a narrow V-shaped configuration. This geometry does not allow entrapment of last-to-freeze platelets in the middle of the sample and consequent lysis from pressure. Instead, the sample freezes from the bottom upward and from the sides to the center. As the volume of the sample increases during freezing, the liquid at the center is squeezed to the upper surface and expands safely on freezing.

Although this device was developed to freeze platelets derived from one unit of PRP, it could be modified to freeze multi-unit preparations obtained either by pooling single-donor units or by plateletpheresis. It has given very reproducible freezing rates of about 30° C. per minute on repeated use. The yield of reconstituted, thawed platelets is similar to that obtained with the nonfrozen control; therefore, there was no indication that the process lyses platelets. In four experiments the yield of platelets was calculated as above 100 percent (Table 1); this is within the limit of experimental error in the platelet counting procedure.

The average recovery of 88.6 percent is an increase of 25 percent over that reported originally, Dayian, G. and Rowe, A. W., *Crybiology* 13, 1 (1976). The increase is due to the deletion of a centrifugation step. Previously, a large volume of a solution containing glycerol (5 g/dl) and glucose (4 g/dl) was added with plasma to a small volume of concentrate in order to minimize osmotic stress. This suspension was centrifuged to reduce the volume of concentrate to be frozen, but some platelets were lost with the supernatant freezing solution. The alternative employed here, subjecting platelets to a greater osmotic stress by mixing equal volumes of platelet suspension and cryoprotectant at twice the final concentration, does not require centrifugation and is no more injurious than exposing platelets to the final concentration of cryoprotectant, as judged by [$^{14}$C]serotonin uptake. This modification saves platelets from mechanical losses and further simplifies the procedure.

Other modifications designed to reduce platelet clumping during thawing and reconstitution include reduction of the thawing temperature from 40° C. to 22° C. and buffering of the freezing solution to pH 6.5 with citrate, which also chelates divalent cations. This shift in the temperature, pH, and divalent cation concentration away from the optima for ADP-induced aggregation [Stoza, L. et al., *Thromb, Diath. Haemorrh.* 18, 713 (1967); Valdorf-Hansen, J. F. and Zucker, M. B., *Amer. J. Physiol.* 220, 105 (1971)] reduced the spontaneous, often irreversible aggregation observed during postthaw processing but did not abolish it. The influence of post-thaw aggregation is shown in Table 2. Of the six units which showed aggregation during thawing and reconstitution, four had a decrease in serotonin uptake. However, in most samples serotonin uptake was only slightly reduced from that obtained by fresh PRP.

One obvious cause of such aggregation is an improper cooling rate that occurred when the outer bag ruptured accidentally (Table 2). Less obvious causes of improper cooling rates have also been detected. When platelets are entrapped in the large entry ports of the UCAR bag, for example, their cooling rate is altered. This was corrected only in part by including 10 ml of air in the freezing bag.

Other factors known to induce post-thaw aggregation are excess amounts of red cells and lipemic plasma. The freezing conditions used for platelets are not optimal for red cells. Since lysed red cells will release ADP, calcium, and other materials injurious to platelets, their concentration must be kept to a minimum. [Gaarder, A., et al., *Nature* 192, 531 (1961)]. When excessive contamination of PRP with red cells is suspended, an additional centrifugation step may be required to remove them.

Exposure of platelets to the freezing solution was in itself somewhat injurious, since nonfrozen platelets took up less serotonin than fresh platelets. Freezing was much more successful, as indicated by the fact that thawed, intact platelets incorporated less serotonin than the nonfrozen, similarly processed platelets. This freeze-thaw injury, however, appears to be reversible, since a longer incubation restored uptake to near normal levels.

Platelets shrink in hypertonic freezing solution and swell when reconstituted in a large volume of plasma. They then, over a period of time, reshape into the disk form. This process, which can be monitored microscopically and spectrophotometrically (unpublished observation), can also be observed by direct inspection. As platelets regain their disc shape, "swirling" can be seen by manipulating them before a bright light. Freezing extends the time it takes platelets to reassume their disc shape as judged by swirling.

The observed reshaping and the restoration of function, which are initiated soon after reconstitution, are strongly suggestive of a competition for energy. Platelets depend upon an intact marginal microtubular bundle maintained by metabolic energy to keep their disc shape. [White, J. G. and Krivit, W., Blood 30, 625 (1967)]. The microtubular structure can be disrupted by osmotic shock [White, J. G., *Amer. J. Path.*, 56, 267 (1969); Zucker-Franklin, D., *J. Clin. Invest.* 48, 165 (1969)] as in the reconstitution step, so that energy would be required to restructure the microtubular system as well as to restore the fluid volume and electrolyte concentration to normal. The microtubular system can also be disrupted by cold, in which case frozen platelets may need to expend additional energy to reassemble it. Such a depletion of energy would affect the platelets' ability to perform other energy-dependent functions, such as serotonin uptake. [Born, G. V. R. and Gillson, R. E., *J. Physiol.* 146, 472 (1959)]. Swirling appears to occur more quickly at 37° C., and this advantage may outweigh the potential danger of aggregation, which would be reduced at 22° C. Another approach could be the use of a synthetic reconstitution medium that would better supply the platelets' metabolic requirements.

If in vivo results are satisfactory, the method should prove useful for routine clinical use. The freezing procedure is simple, the equipment inexpensive, and highly reproducible cooling conditions are easily obtained.

As will be obvious to one skilled in the art, many modifications, variations, alterations and the like may be made in the practices of this invention without departing from the spirit and scope thereof as set forth in the claims which follow.

What is claimed is:

1. A method for cryopreserving cellular suspensions, such as red blood cells, granulocytes and platelets, comprising:
   placing a freezing bag containing the suspension to be preserved and a cryprotective agent between a pair of hinged metal plates including a small angle between them so that the freezing bag assumes wedge shape when viewed from the side,
   placing a layer of thermally insulating material between the metal plates and the freezing bag,
   placing the metal plates with the freezing bag held in position between them in an outer bag, the outer bag being prevented from directly contacting the freezing bag, submerging the outer bag with the metal plates and the freezing bag in a freezing medium; and then transferring the outer bag with the metal plates and the freezing bag to a cryostorage.

2. A method in accordance with claim 1 wherein said freezing bag consists of a plastic material.

3. A method in accordance with claim 2 wherein said plastic material is polyethylene.

4. A method in accordance with claim 1 wherein said outer bag consists of a plastic material.

5. A method in accordance with claim 4 wherein said plastic material is polyethylene.

6. A method in accordance with claim 1 wherein said cryoprotective agent is glycerol-glucose.

7. A method in accordance with claim 1 wherein said freezing medium is liquid nitrogen.

8. A method in accordance with claim 1 wherein said metal plates consist of aluminum.

9. A method according to claim 1 in which the layer of thermally insulating material comprises a pair of thermally insulating plates.

10. A method in accordance with claim 9 wherein said thermally insulating plates consist of cardboard.

11. A device useful in the cryopreservation of cellular suspension, such as red blood cells, granulocytes and platelets which comprises a pair of hinged plates of metal or other material having a high thermal conductivity, said plates being adapted to receive between them a freezing bag and confer a wedge shape when viewed from the side to said freezing bag, and a layer of thermally insulating material receivable between the inner faces of the metal plates and the freezing bag.

12. A device in accordance with claim 11 wherein the insulating material comprises a pair of thermally insulating plates receivable between the inner faces of the metal plates and the freezing bag.

13. A device in accordance with claim 11 wherein said metal plates consist of aluminum.

14. A device in accordance with claim 12 wherein said thermally insulating plates consist of cardboard.

15. A method for cryopreserving cellular suspensions, such as red blood cells, granulocytes and platelets, comprising: placing a plastic freezing bag containing the cellular suspension admixed with a liquid cryoprotective agent between a pair of thermally insulating plates, placing said thermally insulating plates with said freezing bag between a pair of hinged metal plates, the plastic freezing bag containing said cellular suspension being placed between said pair of metal plates so that said pair of metal plates include a small or minor angle therebetween, the pair of metal plates assuming a wedge shape when viewed from the side, affixing together, such as by taping, the pair of metal plates so as to secure the plastic freezing bag containing said cellular suspension therebetween, placing the assembly with a larger outer plastic freezing bag, submerging the resulting assembly in a substantially vertical position within a pool of liquid nitrogen such that the upper surface of the pool of liquid nitrogen is above the top of the plastic freezing bag containing said cellular suspension but below the top of the outer freezing bag such that the liquid nitrogen does not come into direct contact with the plastic freezing bag containing the cellular suspension to be frozen, permitting the resulting assembly to be thus submerged within said liquid nitrogen for a period of time to freeze said cellular suspension and thereupon transferring the resulting assembly, now containing frozen cellular suspension, to the space above the liquid level of said liquid nitrogen for cryostorage.

* * * * *